United States Patent [19]

Bonjouklian

[11] 4,266,049
[45] May 5, 1981

[54] PROCESS FOR 3-IODOMETHYL CEPHALOSPORINS

[75] Inventor: Rosanne Bonjouklian, Indianapolis, Ind.

[73] Assignee: Eli Lilly and Company, Indianapolis, Ind.

[21] Appl. No.: 122,950

[22] Filed: Feb. 20, 1980

[51] Int. Cl.³ .......................................... C07D 501/04
[52] U.S. Cl. ...................................... 544/16; 544/21; 544/17; 544/22
[58] Field of Search ...................... 544/17, 16, 28, 21, 544/22

[56] References Cited

U.S. PATENT DOCUMENTS

| 3,658,799 | 4/1972 | Eardley et al. | 260/243 C |
| 4,042,585 | 8/1977 | Koppel | 544/22 |

OTHER PUBLICATIONS

Karapy et al., Tetrahedron Letters No. 30, pp. 2625-2628.
Jung et al., JACL 99 (3), 968 (1977).
Ho et al., Proc. Natl. Acad. Sci. v & A 75, pp. 4-6, (1970).
Ho et al., Synthesis, 417 (1977).
Morita et al., J. Chem. Soc. Chem. Comm. p. 874 (1970).
Olah et al., Synthesis 583 (1977).
Olah et al., Synthesis 61 (1979).
Mangia et al., Tetrahedron Letters No. 52, pp. 5219-5220 (1978).
Lott et al., J. Chem. Soc. Chem. Comm. 495 (1979).

Primary Examiner—Nicholas S. Rizzo
Attorney, Agent, or Firm—William B. Scanlon; Arthur R. Whale

[57] ABSTRACT

A process for preparing 3-iodomethyl cephalosporins wherein a 3-alkanoyloxymethyl or 3-carbamoyloxymethyl cephalosporin is reacted with a trialkylsilyl iodide, e.g. trimethylsilyl iodide. Certain cephalosporin esters, e.g., benzhydryl esters, undergo cleavage and cephalosporin sulfoxides are reduced to the sulfide form in the process. The 3-iodomethyl cephalosporins are useful intermediates for antibiotics.

20 Claims, No Drawings

PROCESS FOR 3-IODOMETHYL CEPHALOSPORINS

SUMMARY

This invention provides a process wherein 3-alkanoyloxymethyl and 3-carbamoyloxymethyl substituted cephalosporin salts and esters and the sulfoxides thereof are reacted in an aprotic solvent under anhydrous conditions with a tri($C_1$–$C_3$alkyl)silyiodide to form in high yield the corresponding 3-iodomethyl cephalosporin. In the process, certain benzyl and substituted benzyl carboxylic acid protecting ester groups which can be used, e.g. the p-methoxybenzyl and diphenylmethyl esters, undergo cleavage with formation of the tri($C_1$–$C_3$alkyl)silyl ester of the 3-iodomethyl cephalosporin. Other ester groups remain intact under the conditions of the process. Cephalosporin starting materials, when in the sulfoxide form, are reduced to the sulfide form of the 3-iodomethyl product.

The 3-iodomethyl cephalosporins are intermediates useful in the preparation of known 3-substituted-methyl cephalosporin antibiotics.

Cephalosporin compounds substituted in the 3-position by an iodomethyl group have been previously described. For example, Eardley et al., U.S. Pat. No. 3,658,799 teaches the preparation of 3-iodomethyl cephalosporins via the reaction of 3-bromomethyl or 3-chloromethyl cephalosporins with an alkali metal iodide. S. Karady et al., Tetrahedron Letters, No. 30, pp 2625–2628, 1974, describes the preparation of 3-iodomethyl-2-cephem compounds by reacting a 3-acetoxymethyl- or 3-carbamoyloxymethyl-2-cephem with hydriodic acid in a non-polar solvent. U.S. Pat. No. 4,042,585 teaches the preparation of 3-iodomethyl cephalosporins by the reaction of a 3-exomethylenecepham or a sulfoxide thereof with a positive iodinating agent and an alkali metal salt of a $C_1$–$C_7$ alcohol or a bicyclic amidine base.

3-Iodomethyl cephalosporins are known as useful intermediates in the preparation of 3-substituted methyl cephalosporins, for example as taught in U.S. Pat. No. 3,658,799. While the above-described methods for preparing 3-iodomethyl cephalosporins can be used with success, a method for producing these iodomethyl intermediates in higher yields has long been desired by chemists in the cephalosporin art.

BACKGROUND OF THE INVENTION

This invention relates to a process for preparing 3-iodomethyl cephalosporins. In particular, it relates to a process for preparing 3-iodomethyl substituted cephalosporins from 3-acetoxymethyl and 3-carbamoyloxymethyl substituted cephalosporins and a trialkylsilyl iodide.

Trimethylsilyl iodide is known to dealkylate simple alkyl esters of carboxylic acids, M. A. Jung et al., J. Amer. Chem. Soc., 99, 968 (1977), Ho and Olah, Proc. Natl. Acad. Sci. U.S.A. 75 (1978). A mixture of iodine and phenyltrimethylsilane has been described as effective in the deesterification of like esters, Ho and Olah, Synthesis, 417 (1977). Ethers and acetals as well as alkyl esters are dealkylated with trimethylsilyl iodide prepared with chlorotrimethylsilane and sodium iodide, Morita et al., J. Chem. Soc. Chem. Comm. 1978, pp. 874–875. The same reagent has been employed to reduce dialkyl and diphenyl sulfoxides, Olah et al., Synthesis, 583 (1977) and Olah et al., Synthesis, 61 (1979).

DETAILED DESCRIPTION

According to the process of this invention, a cephalosporin compound represented by the following formula 1 is reacted with a trialkylsilyl iodide in an aprotic solvent to provide a 3-iodomethyl cephalosporin represented by the structural formula 2.

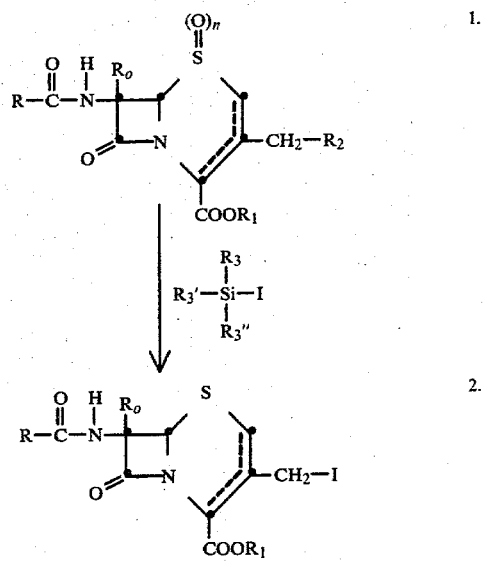

wherein the dotted bonds represent a double bond in either the 2- or 3-position; n is 0 or 1; and when n is 1, the double bond is in the 3-position; R represents the residue of the carboxylic acid forming the acylamino group in the 7-position, and can be any of the 7-acylamino groups of known cephalosporin compounds which are stable under the process conditions of this invention.

The term $R_o$ represents hydrogen or methoxy.

The term $R_1$ in the above formula represents sodium or potassium or an ester group, for example, $C_1$–$C_4$ alkyl, a haloalkyl group, a tri($C_1$–$C_3$ alkyl)silyl group, or an arylmethyl, diarylmethyl, or a substituted arylmethyl or diarylmethyl group.

The term $R_2$ in the above formula 1 represents formyloxy, $C_2$–$C_4$ alkanoyloxy, or a carbamoyloxy group represented by the following structural formula:

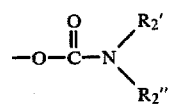

wherein $R_2'$ and $R_2''$ independently are hydrogen or $C_1$–$C_4$ alkyl.

In the above reaction scheme in the formula representing the trialkylsilyl iodide, $R_3$, $R_3'$, and $R_3''$ *independently represent methyl, ethyl or n-propyl*.

The preparation of 3-iodomethyl cephalosporin compounds represented by the formula 2 is carried out in an aprotic solvent under anhydrous conditions at a temperature between about 0° and 35° C. and preferably at between about 20° and about 25° C.

Aprotic solvents which can be employed in the process include the chlorinated hydrocarbon solvents such as chloroform, methylene chloride, 1,2-dichloroethane, 1,1,2-trichloroethane, tetrachloroethane, and like chlorinated hydrocarbon solvents; organo nitriles, for example, acetonitrile and propionitrile; nitroalkanes such as nitromethane and nitroethane; and sulfones, for example, sulfolane. The solvents employed in the process of this invention can be any convenient solvent for the cephalosporin starting material which is unreactive with the silyl iodide. The above-mentioned solvents are commonly employed solvents in the cephalosporin art and can be used in the process of this invention.

In the above formula 1, n represents 0 or 1, indicating the cephalosporin starting material can be either in the sulfide or sulfoxide form. As is shown in the above reaction scheme, where n=1 the sulfoxide group of the starting material is reduced to provide the 3-iodomethyl cephalosporin in the reduced sulfide form represented by the formula 2 (when n=0).

The dotted bonding lines between the 2, 3, and 4-positions of the dihydrothiazine ring of the cephalosporin starting material (formula 1) indicate that the double bond can be located in the 2-position or the 3-position. However, when a cephalosporin sulfoxide is used as starting material (n=1), the double bond in the cephem ring system is located in the 3,4-position. When the starting material is in the sulfide form (n=0), the double bond can be in either the 2,3-position, or the 3,4-position. Accordingly, when a 2-cephem compound represented by the formula 1 is employed in the process of this invention, a 3-iodomethyl-2-cephem compound of the formula 2 is formed. When a 3-cephem compound is employed as starting material either in the sulfide or sulfoxide form, the product represented by the formula 2 is a 3-iodomethyl-3-cephem in the sulfide form.

Because of the high reactivity of the trialkylsilyl iodide with water, the process of this invention is carried out under substantially anhydrous conditions. Accordingly, solvents are preferably dried before use and the trialkylsilyl iodide is kept free of moisture prior to use.

According to the stoichiometry of the reaction occurring in the process, one mole of the trialkylsilyl iodide reacts with one mole of the cephalosporin compound of the formula 1 to provide the 3-iodomethyl cephalosporin of the formula 2. However, the trialkylsilyl iodide can also reduce cephalosporin sulfoxides to the corresponding sulfide form independent of its function as an iodinating agent. Accordingly, when the cephalosporin starting material of the formula 1 is in the sulfoxide form, an additional equivalent of the trialkylsilyl iodide is required. Further, certain esters of cephalosporin compounds are readily cleaved with the trialkylsilyl iodide and, under the anhydrous conditions of the process, form the corresponding trialkylsilyl ester. Accordingly, one equivalent of the trialkylsilyl iodide is required in the process for each of one or more of such reactive esters when present in the starting material, plus one equivalent for the iodination reaction forming the 3-iodomethyl group. Preferably, a molar excess of the trialkylsilyl iodide is used for best yields in the process.

When a cephalosporin starting material (formula 1) is in the sodium or potassium salt form ($R_1$=sodium or potassium) it will be understood that the carboxylate anion and the sodium or potassium cation form the salt. Such salts react under the anhydrous conditions of the process with the trialkylsilyl iodide to form first the trialkylsilyl ester and sodium or potassium iodide. A second molar equivalent of the trialkylsilyl iodide then reacts with the 3-alkanoyloxymethyl or 3-carbamoyloxymethyl substituent to form the corresponding 3-iodomethyl trialkylsilyl ester. Accordingly, as with the ester groups which react preferentially with the silyl iodide, at least two moles of trialkylsilyl iodide are used to convert a cephalosporin sodium or potassium salt of the formula 1 to the 3-iodomethyl trialkylsilyl ester under the conditions of the process.

For example, sodium 7-phenoxyacetamido-3-acetoxymethyl-3-cephem-4-carboxylate is suspended in dry methylene chloride and the suspension is heated at the reflux temperature under an atmosphere of nitrogen. To the warm suspension are added propylene and two equivalents of trimethylsilyl iodide. The reaction is stirred for about eight hours and is then evaporated to dryness. The crude trimethylsilyl 7-phenoxyacetamido-3-iodomethyl-3-cephem-4-carboxylate can then be used to react with a desired heterocyclic thiol to obtain the 3-heterocyclicthiomethyl substituted cephalosporin.

As noted above, certain esters commonly used in the cephalosporin art to protect the carboxylic acid functions present in the molecule react with the trialkylsilyl iodide and undergo cleavage. Such reactive ester groups are included among the arylmethyl and substituted arylmethyl ester groups. Certain of these ester groups, however, are stable depending upon the substituent group. For example, benzyl ester groups substituted in the phenyl ring by a nitro group, for example, the p-nitrobenzyl ester group, are stable to cleavage under the conditions of the process. However, benzyl esters substituted with electron donating groups can undergo cleavage depending upon the strength of the electron donating group. For example, the p-methoxybenzyl ester group is readily cleaved under the conditions of the process, while the p-methylbenzyl ester group is cleaved at a slower rate. The diphenylmethyl ester group is likewise readily cleaved during the process. Such ester groups vary widely in their activity with the trialkylsilyl iodide. Certain reactive esters such as the p-methoxybenzyl and the diphenylmethyl ester undergo cleavage at a much greater rate than the rate of iodination in the 3-position. Other ethers such as the methyl substituted benzyl esters, for example, 4-methylbenzyl and 2,4-dimethylbenzyl esters undergo cleavage at a slower rate, although such rate is competitive with the rate of iodination of the 3-position.

To illustrate the effect of the ortho- and para-directing substituent groups on the cleavage of arylmethyl esters in the process of this invention, the following Table I shows the data obtained via the nuclear magnetic resonance analysis of the reaction products formed when the isomeric ortho-, para-, and meta-methyl benzyl esters of 7-(2-thienylacetamido)-3-acetoxymethyl-3-cephem-4-carboxylic acid were reacted with two equivalents of trimethylsilyl iodide at 20° C. in either methylene chloride or deuterated chloroform in the presence of the hydrogen iodide scavenger, propylene.

TABLE I

| TMSI[1] Cleavage of Isomeric Methylbenzyl esters | | | | | |
|---|---|---|---|---|---|
| | | Ratio of Products[3] | | | |
| Isomer | Time (min.)[2] | A | + B | + | C |
| ortho | 15 min | 2 | 1 | : | 0 |
| | 30 min. | 1 | 0 | : | 3 |
| para | 15 min. | 2 | 1 | : | 0 |
| | 30 min. | 1 | 0 | : | 4 |

TABLE I-continued

| TMSI[1] Cleavage of Isomeric Methylbenzyl esters | | | | | |
|---|---|---|---|---|---|
| | | Ratio of Products[3] | | | |
| Isomer | Time (min.)[2] | A | + B | + | C |
| meta | 15 min. | 1 | : 0 | : | 0 |
| | 180 min. | 0 | : 0 | : | 1 |

[1]Trimethylsilyl iodide
[2]Ratios determined with time via NMR analysis
[3]The products A, B, and C are as shown by the partial formulas:

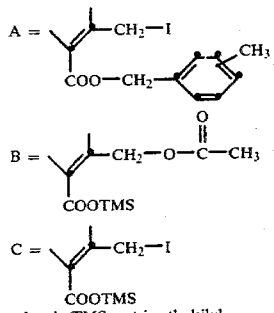

wherein TMS = trimethylsilyl.

As is shown in the above table, both the ortho- and para-methyl substituted benzyl esters undergo cleavage in 15 minutes in competition with the iodination in the 3-position. The meta isomer, however, is stable to cleavage and affords the 3-iodomethyl ester in 15 minutes. The 3-iodomethyl m-methylbenzyl ester required 3 hours to undergo cleavage to provide product C.

Under the reaction conditions employed as described in Table I, the p-methoxybenzyl ester and the diphenylmethyl ester are readily cleaved to provide product C. Other more stable esters such as the benzyl ester and the t-butyl ester require longer reaction times to undergo cleavage. For example, the deesterification of the benzyl ester under the conditions described in Table I requires between about 18 and about 20 hours to obtain product C. The t-butyl ester is cleaved in about 2 to about 3 hours under the same conditions to provide product C. Under the process conditions of this invention, the p-nitrobenzyl ester is virtually unreactive.

The cephalosporin starting material represented by formula 1 can be a silyl ester, for example, a trialkylsilyl ester. Silyl esters of cephalosporin compounds are well known. Commonly, they are prepared by reacting under anhydrous conditions in an aprotic solvent the cephalosporin acid with a silylating agent such as trimethylsilylacetamide (MSA), bistrimethylsilylacetamide, or a hexaalkyldisilazane such as hexamethyldisilazane. Alternatively, the sodium salt of a cephalosporin acid can be reacted with a trialkylsilyl chloride to provide the trialkylsilyl ester. The starting materials employed in the process of this invention, where in the formula 1 $R_1$ is a tri($C_1$-$C_4$-alkyl)silyl group, are prepared with silylating agents by following the known procedures as described above.

The cephalosporin starting material used in the process can be esterified with a conventional ester group commonly employed in the art to protect the $C_4$ carboxylic acid group during reactions without regard to its stability toward the trialkylsilyl iodide. Should the ester group undergo cleavage in competition with the alkanoyloxy or carbamoyloxy group $R_2$ in the 3-position, the cleavage of the ester affords the trialkylsilyl ester formed with the trialkylsilyl iodide. The trialkylsilyl ester thus formed serves the same protecting function served by the original ester group of the starting material. The 3-iodomethyl cephalosporins (formula 2) are intermediates in the preparation of 3-substituted methyl cephalosporins such as 3-heterocyclic thiomethyl substituted cephalosporins. The trialkylsilyl esters of the 3-iodomethyl product, if formed with esters cleaved in the process, are reacted with heterocyclic thiols to form the trialkylsilyl ester of the 3-heterocyclicthiomethyl substituted cephalosporin. The silyl ester is then hydrolyzed to form the desired product in the free acid form.

For example, diphenylmethyl 7β-(2-thienylacetamido)-3-acetoxymethyl-3-cephem-4-carboxylate is reacted in methylene chloride with two equivalents of trimethylsilyl iodide at 25° C. to provide trimethylsilyl 7β-(2-thienylacetamido)-3-iodomethyl-3-cephem-4-carboxylate in solution with the side products, diphenylmethyl iodide and trimethylsilyl acetate. 1-Methyl-1H-tetrazole-5-thiol, dimethylformamide and a hydrogen iodide scavenger, e.g., an alkylene or alkylene oxide such as propylene or propylene oxide, are added to the reaction solution and the nucleophilic displacement reaction of the 3-iodomethyl cephalosporin (product of the process) with the thiol is allowed to proceed at room temperature. The product 7β-(2-thienylacetamido)-3-(1-methyl-1H-tetrazole-5-ylthiomethyl)-3-cephem-4-carboxylic acid is recovered following the hydrolysis of the trimethylsilyl ester group.

As is shown in the above reaction scheme, the trialkylsilyl iodide employed in the process of this invention is represented by the following structural formula.

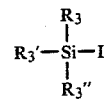

wherein $R_3$, $R_3'$, and $R_3''$ are independently $C_1$-$C_3$ alkyl. Illustrative of the trialkylsilyl iodides of the above formula are trimethylsilyl iodide, triethylsilyl iodide, tri-n-propylsilyl iodide, methyl diethylsilyl iodide, dimethylethylsilyl iodide, methyl ethyl n-propylsilyl iodide, and like $C_1$-$C_3$ alkyl iodides. The trialkylsilyl iodides employed in the process of this invention are prepared by normal procedures and are highly reactive substances. They react readily with active hyrogen-containing compounds to form the silyl derivatives thereof. The preferred trialkylsilyl iodide of this invention is trimethylsilyl iodide TMSI. The higher alkylsilyl iodides, for example, triethylsilyl iodide, are less reactive in the process of this invention and thus require longer reaction times to achieve the desired yield of product.

The process of this invention is preferably carried out in the presence of a hydrogen iodide scavenger. Preferred scavengers include alkylenes, dienes, and alkylene oxides, and preferably the low molecular weight alkylenes which on reaction with hydrogen iodide form volatile alkyl iodides. The scavenger functions to remove any hydrogen iodide which is present in the reaction, for example, by virtue of there being a slight molar excess of the trimethylsilyl iodide present in the reaction medium or trace amounts in the reagent. The removal of the hydrogen iodide provides a cleaner reaction product, although the reaction proceeds in the absence of a scavenger. Preferred scavengers of this invention are the lower molecular weight olefins such as ethylene, propylene, butylene, amylene, and like olefins; the dienes, for example, butadiene, pentadiene, cyclopentadiene, cyclohexadiene, and the like. Preferred alkylene oxides are propylene oxide and butylene oxide. Because of the higher volatility of the lower alkyl iodides, the especially preferred olefins for use in this invention are ethylene and propylene. Ethylene is a desirable scavenger for use in large scale manufacturing equipment where it is possible to apply pressure to the reaction vessel with ease. Alternatively, a stream of ethylene gas can be passed through the reaction mixture to maintain a sufficient level of the scavenger during the process.

As previously described herein, the starting material represented by the formula 1 can be substituted in the 7-position by 7-acylamino substituents of known cephalosporin compounds.

In the starting materials employed in the process (formula 1) the 7-acylamino side chain,

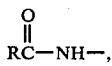

can be any of a large number of acylamino groups present in the known cephalosporin compounds. For example, R in the formula 1 can be alkyl of 1 to 6 carbon atoms; haloalkyl, cyanoalkyl; an aryl group, e.g., phenyl or substituted phenyl such as nitrophenyl, methylphenyl, hydroxyphenyl, halophenyl, aminophenyl, lower alkoxyphenyl, wherein the phenyl is substituted with from one to three of such substituent groups; or an aryl, e.g., phenyl, substituted methyl group or a heteroarylmethyl group.

Preferably the term R is a substituted methyl group such as benzyl, α-hydroxybenzyl, α-aminobenzyl, α-carboxybenzyl, 3- or 4-hydroxy-α-aminobenzyl, 3- or 4-hydroxy-α-carboxybenzyl, phenoxymethyl, 2-thienylmethyl, 2-furylmethyl, 2-aminothiazolylmethyl, 2-aminothiazolyl-α-methoxyiminomethyl, and 1-tetrazolylmethyl.

The term $R_0$ in formula 1 represents hydrogen or methoxy.

The term $R_1$ in formula 1 represents a carboxylic acid protecting ester group or a sodium or potassium cation. Numerous ester groups are commonly used in the cephalosporin art to protect the $C_4$ carboxylic acid function as well as other carboxylic acid functions situated elsewhere in the cephalosporin molecule, for example, in the 7-position side chain. For example, the carboxy group can be attached to the phenyl group of the phenylacetyl side chain or in the α-position of the phenylacetyl side chain. Ester groups which are commonly used include, for example, t-butyl; methoxymethyl; haloalkyl, such as iodomethyl, 2,2,2-trichloroethyl and 2,2,2-tribromoethyl; benzyl and substituted benzyl esters, for example, p-methoxybenzyl, p-nitrobenzyl, methylbenzyl, 3,5-di-t-butyl-4-hydroxybenzyl; diphenylmethyl and substituted diphenylmethyl groups such as 4-methoxydiphenylmethyl, 4,4'-dimethoxydiphenylmethyl, and 4-hydroxydiphenylmethyl; and silyl groups such as trialkylsilyl, for example, trimethylsilyl. These ester groups are characterized by their lability to hydrolysis under acid or basic conditions or under reductive cleavage conditions such as with nascent hydrogen or by catalytic hydrogenolysis.

The term $R_2$ in the formula 1 represents formyloxy or $C_2$–$C_4$ alkanoyloxy, for example, acetoxy, propionyloxy or butyryloxy; or a carbamoyloxy or substituted carbamoyloxy group such as methylcarbamoyloxy, dimethylcarbamoyloxy, diethylcarbamoyloxy, methylethyl-carbamoyloxy, n-butylcarbamoyloxy, and like mono or disubstituted carbamoyloxy groups.

These 7-acylamino groups are stable under the process conditions of this invention. However, certain functional groups which are commonly attached to the 7-acylamino substituent of cephalosporins can interfere with the iodination reaction by virtue of their reactivity towards the trialkylsilyl iodide reagent. For example, any hydroxy, amino, or carboxylic acid functions in the side chain can be protected in the starting material prior to use in the process.

With respect to amino-protecting groups, commonly used protecting groups which form urethanes react with trialkylsilyl iodides to form the unprotected amino group, which in turn can react with the iodinating agent causing untoward side products. Accordingly, protecting groups which form urethanes are not desirably employed as amino-protecting groups for the starting materials. Protecting groups such as t-butyloxycarbonyl, benzyloxycarbonyl, p-nitrobenzyloxycarbonyl, and trichloroethoxycarbonyl, which form urethanes with amino substituents, are preferably not used. Other types of amino-protecting groups are, however, useful in the process of this invention when it is desired to retain the protecting group intact during the preparation of the 3-iodomethyl substituted cephalosporin and its subsequent use as an intermediate. Preferred protecting groups which can be employed to protect any free amino groups present include the trityl group, trialkylsilyl groups, and enamines formed with β-dicarbonyl compounds.

For free hydroxy groups present in the molecule, protecting groups which can be used include the trityl group, $C_1$–$C_4$ alkanoyl esters, and trialkylsilyl ether derivatives.

Any free carboxylic acid functions, for example, in the α-position of a 7-acetamido side chain can be protected by the esters employed for protecting the carboxylic acid function in the 4-position of the cephalosporin molecule ($R_1$, formula 1). For example, the carboxy group in the side chain, i.e., α-carboxyphenylacetamido, can be protected with a silyl ester, a benzyl ester, a t-butyl ester, a p-nitrobenzyl ester, and like esters as described above.

Although any hydroxy and carboxy groups present in the starting material are desirably protected when the 3-iodomethyl substituted product is to be used in subsequent reactions, under the anhydrous conditions of the process the hydroxy and carboxy groups can be protected beforehand as trialkylsilyl ethers and esters, respectively. As is the case with the $C_4$ carboxy group, an esterified carboxy group present elsewhere in the starting material (which is a trialkylsilyl iodide reactive ester) can undergo deesterification during the process of this invention with formation of the trialkylsilyl ester in situ. Thus, the carboxy group is protected although not with the original protecting group.

A preferred group of starting materials which can be employed in the process of this invention are represented by the above formula 1, wherein R is hydrogen, $C_1$–$C_4$ alkyl, cyanomethyl, halomethyl, or a group represented by the formula

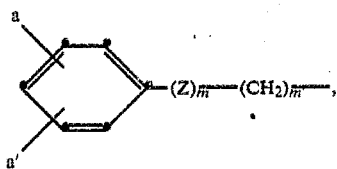

wherein
a and a' are independently hydrogen, carboxy, carboxymethyl, protected aminomethyl or halogen, $C_1$–$C_3$ alkyl, or $C_1$–$C_3$ alkoxy; Z is O or S; m and m' are 0 or 1; and when m is 1, m' is 1;

or R is a heteroarylmethyl group represented by the formula $$R'—CH_2—$$

wherein R' is

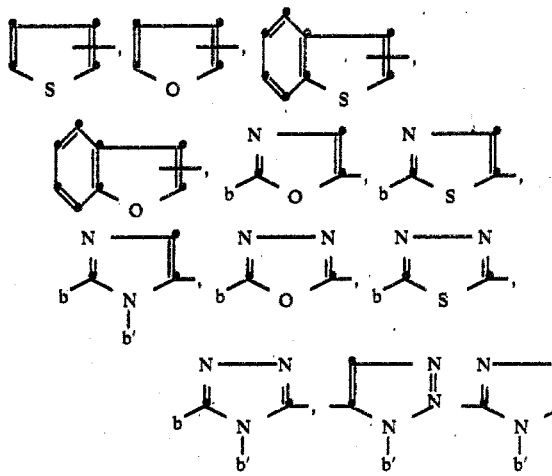

wherein
b is H, $C_1$–$C_3$ alkyl, or protected $NH_2$;
and b' is H, or $C_1$–$C_3$ alkyl;

or R is an α-substituted arylmethyl or heteroarylmethyl group represented by the formula

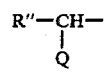

wherein
R'' is thienyl, furyl, cyclohexenyl, 1,4-cyclohexadienyl, phenyl, or substituted phenyl substituted by $C_1$–$C_3$ alkyl, $C_1$–$C_3$ alkoxy, halogen, or hydroxy, and,
Q is protected-hydroxy, protected-amino, or protected-carboxy;

or R is an α-oximino group represented by the formula

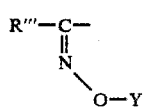

wherein R''' is R'' as defined above or the group of the formula

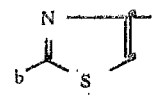

wherein
b is H, $C_1$–$C_3$ alkyl or protected $NH_2$;
Y is hydrogen, $C_1$–$C_4$ alkyl, $C_1$–$C_4$ haloalkyl, $C_2$–$C_4$ alkenyl, benzyl, $C_2$–$C_4$ alkanoyl, phenylsulfonyl, or $C_1$–$C_4$ alkylsulfonyl;
$R_0$ is hydrogen or methoxy;
$R_1$ is $C_1$–$C_4$ alkyl, 2,2,2-trichloroethyl, iodomethyl, diphenylmethyl, benzyl, substituted benzyl substituted by methyl, methoxy or nitro; or $R_1$ is a trialkylsilyl group represented by the formula

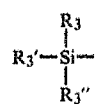

wherein
$R_3$, $R_3'$, and $R_3''$ are independently $C_1$–$C_3$ alkyl;
or $R_1$ is sodium or potassium;
$R_1'$ has the same meanings as $R_1$, provided that, when $R_1$ is diphenylmethyl, or p-methoxybenzyl, $R_1'$ is

$R_2$ is $C_1$–$C_4$ alkanoyloxy or a carbamoyloxy group represented by the formula

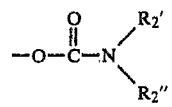

wherein
$R_2'$ and $R_2''$ are independently hydrogen or $C_1$–$C_3$ alkyl; and
n is 0 or 1;
with the limitation that when n is 1, the double bond represented by the dotted bonding lines is in the 3-position.

In the above definition the term $C_1$–$C_4$ alkyl refers to methyl, ethyl, n-propyl, iso-propyl, n-butyl, iso-butyl, sec-butyl, and t-butyl; halogen refers to fluoro, chloro, bromo, and iodo; $C_1$–$C_3$ alkoxy refers to methoxy, ethoxy, n-propoxy, and iso-propoxy; protected-hydroxy refers to the hydroxy group wherein the hydrogen is replaced with a trityl group, $C_1$–$C_4$ alkanoyl, and tri($C_1$–$C_3$ alkyl)silyl; protected-amino refers to the amino group substituted by trityl, an enamine group formed with methyl acetoacetate or ethyl acetoacetate, and tri($C_1$–$C_3$ alkyl)silyl; protected-carboxy refers to the esterified carboxy group wherein the ester moiety is $C_1$–$C_4$ alkyl, benzyl, methylbenzyl, p-methoxybenzyl, p-nitrobenzyl, diphenylmethyl, iodomethyl, 2,2,2-trichloroethyl, or tri($C_1$–$C_3$ alkyl)silyl.

Illustrative of the groups represented by R in the above defined preferred starting materials when R is $C_1$–$C_4$ alkyl, are methyl, ethyl; haloalkyl is bromomethyl, chloromethyl; and when R is

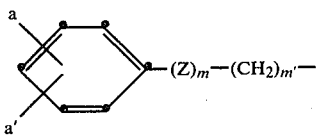

R can be, for example, phenyl, benzyl, p-hydroxybenzyl, p-chlorobenzyl, 3,4-dimethoxybenzyl, 2-methylbenzyl, 3-methylbenzyl, phenoxymethyl, p-chlorophenoxymethyl, phenylmercaptomethyl, 3,4-dichlorophenylmercaptomethyl, 4-fluorophenylmercaptomethyl, or 3,5-dichlorophenylmercaptomethyl; and when R is R'—CH$_2$—, R is, for example, 2-thienylmethyl, 3-thienylmethyl, 2-furylmethyl, benzothien-2-ylmethyl, benzofur-2-ylmethyl, 1,3-oxazol-5-ylmethyl, 2-methyl-1,3-oxazol-5-ylmethyl, 1,3-thiazol-5-ylmethyl, 2-amino-1,3-thiazol-4-ylmethyl, 1,2-dimethylimidazol-5-ylmethyl, 2-aminoimidazol-5-ylmethyl, 2-methyl-1,3,4-oxadiazol-5-ylmethyl, 2-ethyl-1,3,4-oxadiazol-5-ylmethyl, 1,3,4-thiadiazol-5-ylmethyl, 2-methyl-1,3,4-thiadiazol-5-ylmethyl, 1,2-dimethyl-1,3,4-triazol-5-ylmethyl, 1-methyl-1,3,4-triazol-5-ylmethyl, 1,2,3-triazol-5-ylmethyl, 1-methyl-1,2,3-triazol-5-ylmethyl, 1-methyltetrazol-5-ylmethyl, or 1-isopropyltetrazol-5-ylmethyl; and when R is R''—CH(Q)—, and Q is amino, R can be, for example, α-aminobenzyl, α-amino-4-hydroxybenzyl, α-amino-3-hydroxybenzyl, α-amino-4-methoxybenzyl, α-amino-2-thienylmethyl, α-amino-3-thienylmethyl, α-amino-1,4-cyclohexadienylmethyl, wherein the amino group is substituted with an amino-protecting group, and when Q is hydroxy, R can be α-hydroxybenzyl, α-hydroxy-2-thienylmethyl, α-hydroxy-2-furylmethyl, or α-hydroxycyclohexenylmethyl wherein the hydroxy group is optionally protected; and when Q is carboxy, R can be, for example, α-carboxybenzyl, α-carboxy-4-hydroxybenzyl, α-carboxy-3-hydroxybenzyl, and α-carboxy-4-methoxybenzyl, wherein the carboxy group is protected. Examples of R groups in the formula when R is an α-oximino group of the formula

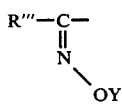

are α-methoxyiminobenzyl, α-methoxyimino-2-furylmethyl, α-methoxyimino-2-thienylmethyl, α-methoxyimino-2-aminothiazol-4-ylmethyl, α-acetoxyiminobenzyl, α-chloroacetoxyimino-2-furylmethyl, α-methanesulfonyloxyiminobenzyl, α-phenylsulfonyloxyimino-2-furylmethyl, α-acetoxyimino-2-aminothiazol-4-ylmethyl, α-chloroacetoxyimino-2-aminothiazol-4-ylmethyl, α-methoxyimino-2-tritylaminothiazol-4-ylmethyl, α-trimethylsilyloxyimino-2-furylmethyl, α-methanesulfonyloxyimino-2-aminothiazol-4-ylmethyl, and the amino-protected derivatives thereof when a free amino group is present.

Representative of the groups R$_2$ are acetoxy, propionoxy, butryloxy, carbamoyloxy, N-methylcarbamoyloxy and, N,N-dimethylcarbamoyloxy.

Preferred compounds are represented by the formula 1 when n is O, R$_2$ is acetoxy or carbamoyloxy, and the cephalosporins have the double bond in the 3-position (3-cephem). A preferred ester group is the p-nitrobenzyl ester group. Another preferred ester group is the trimethylsilyl group.

A further preferred group of 3-iodomethyl cephalosporins produced in the process of this invention and which are represented by the formula 2 are p-nitrobenzyl 7-phenylacetamido-3-iodomethyl-3-cephem-4-carboxylate, benzyl 7-phenylacetamido-3-iodomethyl-3-cephem-4-carboxylate, p-nitrobenzyl 7-phenoxyacetamido-3-iodomethyl-3-cephem-4-carboxylate, p-nitrobenzyl 7-(2-thienylacetamido)-3-iodomethyl-3-cephem-4-carboxylate, p-nitrobenzyl 7-methoxy-7-(2-thienylacetamido)-3-iodomethyl-3-cephem-4-carboxylate, trimethylsilyl 7-(1-tetrazolacetamido)-3-iodomethyl-3-cephem-4-carboxylate, benzyl 7-(α-hydroxy-α-phenylacetamido)-3-iodomethyl-3-cephem-4-carboxylate, trimethylsilyl 7-[syn-2-(2-tritylaminothiazol-4-yl)-2-methoxyiminoacetamido]-3-iodomethyl-3-cephem-4-carboxylate, p-nitrobenzyl 7-[syn-2-(2-trimethylsilylaminothiazol-4-yl)2-methoxyiminoacetamido]-3-iodomethyl-3-cephem-4-carboxylate, and benzyl 7-methoxy-7-phenylacetamido-3-iodomethyl-3-cephem-4-carboxylate.

A preferred group of starting materials of the formula 1 for use in the process are p-nitrobenzyl 7-phenoxyacetamido-3-acetoxymethyl-3-cephem-4-carboxylate, benzyl 7-(2-thienylacetamido)-3-acetoxymethyl-3-cephem-4-carboxylate, p-nitrobenzyl 7-methoxy-7-(2-thienylacetamido)-3-carbamoyloxymethyl-3-cephem-4-carboxylate, p-nitrobenzyl 7-(2-thienylacetamido)-3-acetoxymethyl-3-cephem-4-carboxylate, benzyl 7-methoxy-7-phenylacetamido-3-acetoxymethyl-3-cephem-4-carboxylate, trimethylsilyl 7-phenoxyacetamido-3-acetoxymethyl-3-cephem-4-carboxylate, p-nitrobenzyl 7-phenylacetamido-3-carbamoyloxymethyl-3-cephem-4-carboxylate, t-butyl 7-(2-thienylacetamido)-3-acetoxymethyl-3-cephem-4-carboxylate, methyl 7-methoxy-7-(2-thienylacetamido)-3-acetoxymethyl-3-cephem-4-carboxylate, trimethylsilyl 7-[syn-2-(tritylaminothiazol-4-yl)-2-methoxyiminoacetamido]-3-acetoxymethyl-3-cephem-4-carboxylate, and diphenylmethyl 7-phenylacetamido-3-acetoxymethyl-3-cephem-4-carboxylate.

The starting materials of the formula 1 and the 3-iodomethyl cephalosporin products of the formula 2 have the conventional cephalosporin configuration. The 7-position side chain has the β-configuration and the hydrogen or methoxy group, R$_0$, in the 7-position has the α-configuration. In the compounds having an oximino group in the α-position of the side chain, the oximino group can be in either the syn or anti form and preferably the syn form.

The following examples further illustrate the process of this invention. In the examples the nuclear magnetic resonance spectra (NMR) were obtained on a Varian Associates T-60 Spectrometer using tetramethylsilane as the reference standard. The chemical shifts are expressed in delta values in ppm and coupling constants (J) are expressed in cycles per second (cps). The signals are identified as follows: s=singlet, d=doublet, q=quartet, and m=multiplet.

Infrared spectra (IR) were determined using a Beckman Acculab 3 Spectrometer.

Mass Spectra were determined using a Varian MAT 731 Spectrometer.

All reactions employing trimethylsilyliodide (TMSI) were carried out under a nitrogen atmosphere in flame-dried flasks.

EXAMPLE 1 p-Nitrobenzyl 7β-phenoxyacetamido-3-iodomethyl-3-cephem-4-carboxylate

To a solution of 241 mg of p-nitrobenzyl 7β-phenoxyacetamido-3-acetoxymethyl-3-cephem-4-carboxylate in 3 ml of methylene chloride was rapidly added 0.14 ml of trimethylsilyl iodide and the mixture stirred for about 1 hour at room temperature. The course of the reaction is followed by thin layer chromatography.

The deep orange reaction mixture was transferred to a separatory funnel, diluted with additional methylene chloride, and was washed successively with ice cold aqueous solutions of 10% sodium thiosulfate, 10% sodium bicarbonate, and with saturated sodium chloride. The reaction mixture was dried over anhydrous magnesium sulfate, filtered, and evaporated to dryness under reduced pressure in a cold water bath. The product, p-nitrobenzyl 7β-phenoxyacetamido-3-iodomethyl-3-cephem-4-carboxylate, was obtained as a golden solid in 92% yield (0.25 g).

The infrared spectrum of the product run in deuterated chloroform as a film showed the following absorption maxima: 1771, 1715, and 1678 $cm^{-1}$.

The nuclear magnet resonance spectrum of the product run is deuterated chloroform showed the following signals: 5.88 (q, J=6 Hz and 10 Hz, $C_7$—H), 5.40 (s, ester $CH_2$, 2H), 5.05 (d, J=6 Hz, $C_6$—H), 4.55 (s, phenoxy-$CH_2$, 2H), 4.40 (s, $CH_2I$, 2H), 3.65 (ABq, J=19 Hz, $C_2$—H).

The field desorption mass spectrum of the product showed the following mass ions: $(M+1)^+ = 610$, $(M-127)^+ = 482$.

EXAMPLE 2

Benzyl 7β-phenylacetamido-3-iodomethyl-3-cephem-4-carboxylate

By following the procedure and conditions employed as described in Example 1, 812 mg of benzyl 7β-phenylacetamido-3-acetoxymethyl-3-cephem-4-carboxylate were reacted in 10 ml of methylene chloride with 0.53 ml of trimethylsilyl iodide at 20° C. The 3-iodomethyl benzyl ester was obtained as a pale orange solid at 96% yield (0.9 g).

The infrared spectrum of the above product run in deuterated chloroform as a film showed the following absorption maxima: 1775, 1715, 1670 $cm^{-1}$.

The nuclear magnetic resonance spectrum of the above product run in deuterated chloroform showed the following signals: 7.2–7.4 (aromatic, 10H), 4.60 (d, J=9 Hz, NH), 5.68 (q, J=5 Hz and 9 Hz, $C_7$—H), 5.21 (s, ester $CH_2$, 2H), 4.85 (d, J=5 Hz, $C_6$-H), 4.32 (s, $Ch_2I$, 2H), 3.55 (s, amide $CH_2$, 2H), and 3.5 (ABq, J=19 Hz, $C_2$—H, 2H).

The field desorption mass spectrum of the above product showed the following ions: $(M+1)^+ = 549$, $(M-127)^+ = 421$.

EXAMPLE 3

Benzyl 7α-methyoxy-7β-phenylacetamido-3-iodomethyl-3-cephem-4-carboxylate

By following the procedures and conditions described in Example 1, 330 mg of benzyl 7α-methoxy-7β-phenylacetamido-3-acetoxymethyl-3-cephem-4-carboxylate dissolved in 4 ml of methylene chloride was reacted with 0.2 ml of trimethylsilyl iodide at about 20° C. for 1 hour. The 3-iodomethyl benzyl ester was isolated as a golden solid in 95% yield (0.36 g).

The infrared spectrum of the above product run in deuterated chloroform as a film showed the following absorption maxima: 1770, 1717, 1680 $cm^{-1}$.

The NMR spectrum of the above product run in deuterated chloroform showed the following signals: 7.1–7.4 (aromatic, 10H), 6.58 (s, NH, 1H), 5.27 (s, ester $CH_2$, 2H), 5.0 (s, $C_6$—H), 4.32 (s, $CH_2I$, 2H), 3.66 (s, amide $CH_2$, 2H), 3.39 (s, $OCH_3$), 3.4 (buried broad multiplet, $C_2$—H).

The field desorption mass spectrum of the above product showed the following mass ions: $M^+ = 578$, $(M-127)^+ = 451$.

EXAMPLE 4 t-Butyl 7β-(2-thienylacetamido)-3-iodomethyl-2-cephem-4-carboxylate

By following the procedures and reaction conditions employed in Example 1, a solution of 313 mg of t-butyl 7β-(2-thienylacetamido)-3-acetoxymethyl-2-cephem-4-carboxylate in 4 ml of methylene chloride was reacted with 0.188 ml of trimethylsilyl iodide at 20° C. The 3-iodomethyl-2-cephem ester was obtained in 61% yield (0.22 g).

The infrared absorption spectrum of the above product run in deuterated chloroform as a film showed the following absorption maxima: 1770, 1728, and 1665 $cm^{-1}$.

The NMR spectrum of the above product run in deuterated chloroform showed the following signals: 6.9–7.2 (thienyl H, 3H), 6.47 (broad s, $C_2$—H), 5.59 (q, J=4 Hz and 9 Hz, $C_7$—H), 5.21 (d, J=4 Hz, $C_6$—H), 5.17 (s, $C_4$—H), 4.19 (ABq, J=10 Hz, $CH_2I$), 3.81 (s, amide $CH_2$), and 1.5 (s, $CH_3$, 9H).

The field desorption mass spectrum of the above product showed the following mass ions: $(M+1)^+ = 521$, $(M-127)^+ = 393$.

EXAMPLE 5

Methyl 7α-methoxy-7β-(2-thienylacetamido)-3-iodomethyl-3-cephem-4-carboxylate To a solution of 30 mg (0.068 mmole) of methyl 7α-methoxy-7β-(2-thienylacetamido)-3-carbamoyloxymethyl-3-cephem-4-carboxylate in 1 ml of deuterochloroform in an NMR tube was rapidly added 0.01 ml (0.075 mmole) of trimethylsilyl iodide. Within 5 minutes at 20° C. the reaction was complete as demonstrated by the NMR spectrum of the reaction mixture.

The contents of the tube were diluted with chloroform and the solution transferred to a separatory funnel. The solution was washed successively with ice cold aqueous solutions of 10% sodium thiosulfate, 10% sodium bicarbonate, and with saturated sodium chloride. The solution was dried over anhydrous sodium sulfate, filtered and evaporated to dryness under reduced pressure. The 3-iodomethyl methyl ester was obtained in 90% yield (0.033 g) as a pale gold solid. The infrared absorption spectrum of the above product run in chloroform as a film showed the following absorption maxima: 1762, 1718, and 1685 $cm^{-1}$.

The NMR spectrum of the above product run in deuterated chloroform showed the following signals:

6.9–7.3 (thiophene CH), 5.02 (s, $C_6$—H), 4.38 (broad s, $CH_2I$), 3.82 (s, side chain $CH_2$), 3.80 (s, ester $CH_3$), and 3.41 (broad s, $C_2$—H and $OCH_3$).

EXAMPLE 6

7β-(2-Thienylacetamido)-3-(1-methyl-1H-tetrazole-5-ylthiomethyl)-3-cephem-4-carboxylic acid via trimethylsilyl 7β-(2-thienylacetamido)-3-iodomethyl-3-cephem-4-carboxylate To a suspension of 0.836 g (2 mmole) of sodium 7β-(2-thienylacetamido)-3-acetoxymethyl-3-cephem-4-carboxylate (sodium cephalothin) in 40 ml of dry methylene chloride maintained at the reflux temperature under a nitrogen atmosphere were added 0.7 ml (5.5 mmole) of chlorotrimethylsilane. The silylation of the $C_4$ carboxy group was allowed to proceed 18 hours and the resulting yellow suspension was cooled to room temperature. The suspension was then reduced in volume by one-half under reduced pressure and 0.56 ml (4 mmole) of trimethylsilyl iodide were added rapidly. The color of the suspension gradually changed to a deep orange over one hour at room temperature. After 1.5 hours, 3 ml of dry dimethylformamide and 1 ml of propylene oxide were added to the orange suspension followed by 0.4 g (3.4 mmole) of 1-methyltetrazole-5-thiol. The reaction of the tetrazole thiol with the 3-iodomethyl derivative was allowed to proceed at room temperature for one hour after which 20 ml of methylene chloride and 20 ml of cold dilute hydrochloric acid (pH2) were added to the black reaction solution. The mixture was stirred vigorously for 20 minutes, was filtered and the organic layer separated. The organic layer was washed repeatedly with cold brine, dried over sodium sulfate and was filtered. Concentration of the organic layer afforded trimethylsilyl 7β-(2-thienylacetamido)-3-(1-methyl-1H-tetrazole-5-ylthiomethyl)-3-cephem-4-carboxylate contaminated with some DMF and 2-iodo-1-trimethylsilylpropanol.

The trimethylsilyl ester group of the product was removed as follows. The product was dissolved in about 200 ml of chloroform and a mixture of ice and a saturated aqueous solution of sodium bicarbonate were addd gradually to the solution over a two-hour period until the pH was maintained at about 7.9–8.0. The aqueous phase was separated and was carefully acidified to pH 3.2 with dilute hydrochloric acid in the presence of ethyl acetate. The aqueous phase was washed several times with ethyl acetate and the washings were combined with the organic layer. The combined organic layer was washed with brine, dried over sodium sulfate, filtered and concentrated under reduced pressure. The product was the free acid, 7β-(2-thienylacetamido)-3-(1-methyl-1H-tetrazole-5-ylthiomethyl)-3-cephem-4-carboxylic acid, was filtered from the concentrate. There were obtained 0.70 g (77% yield) of the product which was identical with an authentic sample.

The NMR spectrum of the product run in $CDCl_3$, $d_6$-DMSO, 4:1, v:v, showed the following signals: 7.2 and 6.96 (2 m, 3H), 5.7 (ABq, 1H), 5.0 (d, 1H), 4.32 (s, 2H), 3.96 (s, 3H), and 3.75 (m, 4H) delta.

The product run on a silica gel chromatogram using ethyl acetate:acetic acid, 4:1, v:v had an Rf of 0.45.

EXAMPLE 7

Methyl 7β-[syn-2-(2-tritylaminothiazol-4-yl)-2-methoxyiminoacetamido]-3-iodomethyl-3-cephem-4-carboxylate To an NMR tube were added 0.75 ml of deuterochloroform and 0.071 g (0.1 mmole) of methyl 7β-[syn-2-(2-tritylaminothiazol-4-yl)-2-methoxyiminoacetamido]-3-acetoxymethyl-3-cephem-4-carboxylate. Propene gas was gently bubbled in to the solution followed by the addition of 0.032 ml (0.22 mmole) of trimethylsilyliodide. The reaction was monitored by NMR analysis and was complete in about 3.5 hours.

The reaction mixture was diluted with cold methylene chloride, transferred to a spearatory funnel, and washed sequentially with a cold dilute aqueous solution of sodium bisulfite, a cold dilute aqueous solution of sodium bicarbonate, and with cold brine. The organic layer was separated, dried over sodium sulfate, filtered after drying, and concentrated under vacuum. The product was filtered from the concentrate in substantially pure form. There were obtained 0.059 g (76% yield).

NMR spectrum ($CDCl_3$): 6.66 (d, 1H, amide NH), 6.48 (s, 1H), 5.92 (ABq, 1H), 4.98 (d, 1H), 4.35 (broad s, 2H), 4.05 (s, 3H), 3.83 (s, 3H) and, 3.60 (ABq, 2H) delta.

IR spectrum (methylene chloride film): 1780 $cm^{-1}$, 1730 $cm^{-1}$, 1690 $cm^{-1}$ (broad) and, 1672 $cm^{-1}$.

Field Desorption Mass Spectrum: $M^+ = 779$, $(M-1)^+ = 778$, $(M-127)^+ = 652$ and $(M-128)^+ = 651$.

I claim:

1. A process for preparing a 3-iodomethyl cephalosporin of the formula

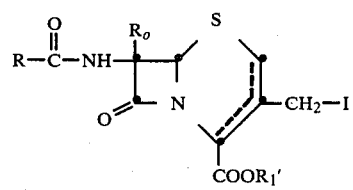

which comprises reacting in an aprotic solvent under substantially anhydrous conditions at a temperature between about 0° C. and about 35° C. a 3-alkanoyloxymethyl or 3-carbamoyloxymethyl cephalosporin of the formula

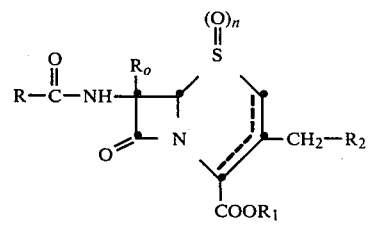

with a trialkylsilyl iodide of the formula

where in the above formulas R is hydrogen, $C_1$-$C_4$ alkyl, cyanomethyl, halomethyl, or a group of formula

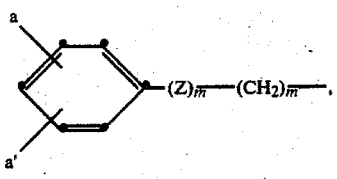

wherein
a and a' are independently hydrogen, carboxy, carboxymethyl, protected aminomethyl or halogen, $C_1$-$C_3$ alkyl, or $C_1$-$C_3$ alkoxy;
Z is O or S; m and m' are 0 or 1;
and when m is 1, m' is 1;
or R is a heteroarylmethyl group of the formula

R'—CH$_2$— wherein R' is

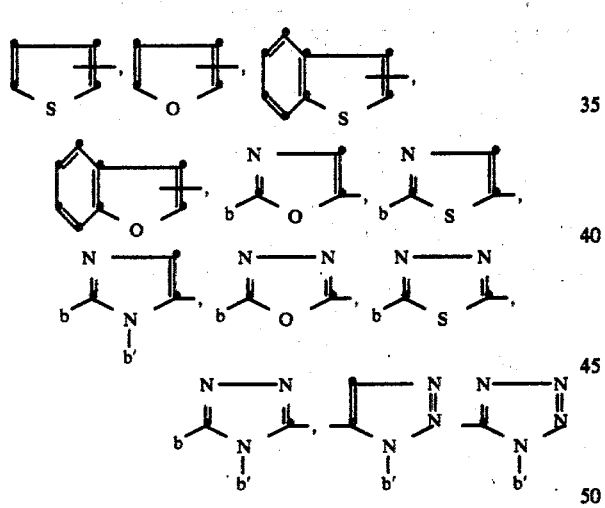

wherein
b is H, $C_1$-$C_3$ alkyl, or protected NH$_2$;
and b' is H, or $C_1$-$C_3$ alkyl;
or R is an α-substituted arylmethyl or heteroarylmethyl group of the formula

wherein
R'' is thienyl, furyl, cyclohexyl, 1,4-cyclohexadienyl, phenyl, or substituted phenyl substituted by $C_1$-$C_3$ alkyl, $C_1$-$C_3$ alkoxy, halogen, or hydroxy, and,
Q is protected-hydroxy, protected-amino, or protected-carboxy;
or R is an α-oximino group of the formula

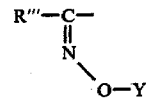

wherein R''' is R'' as defined above or the group of the formula

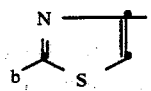

wherein
b is H, $C_1$-$C_3$ alkyl or protected NH$_2$;
Y is hydrogen, $C_1$-$C_4$ alkyl, $C_1$-$C_4$ haloalkyl, $C_2$-$C_4$ alkenyl, benzyl, $C_2$-$C_4$ alkanoyl, phenylsulfonyl, or $C_1$-$C_4$ alkylsulfonyl;
R$_o$ is hydrogen or methoxy;
R$_1$ is $C_1$-$C_4$ alkyl, 2,2,2-trichloroethyl, iodomethyl, diphenylmethyl, benzyl, substituted benzyl substituted by methyl, methoxy or nitro; or R$_1$ is a trialkylsilyl group of the formula

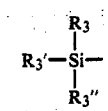

wherein
R$_3$, R$_3$', and R$_3$'' are independently $C_1$-$C_3$ alkyl;
or R$_1$ is sodium or potassium;
R$_1$' has the same meanings as R$_1$, provided that, when R$_1$ is sodium, potassium, diphenylmethyl, or p-methoxybenzyl,
R$_1$' is

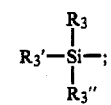

R$_2$ is $C_1$-$C_4$ alkanoyloxy or a carbamoyloxy group of the formula

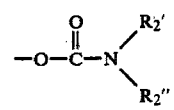

wherein
R$_2$' and R$_2$'' are independently hydrogen or $C_1$-$C_3$ alkyl; and
n is 0 or 1;
with the limitation that when n is 1, the double bond represented by the dotted bonding lines is in the 3-position.

2. The process of claim 1 wherein the trialkylsilyl iodide is trimethylsilyl iodide.

3. The process of claim 2 wherein R is a group of the formula

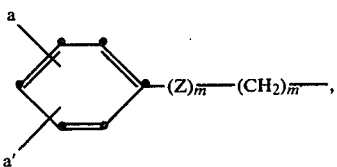

4. The process of claim 3 wherein $R_2$ is $C_1$–$C_4$ alkanoyloxy.

5. The process of claim 4 wherein p-nitrobenzyl 7β-phenoxyacetamido-3-acetoxymethyl-3-cephem-4-carboxylate is reacted.

6. The process of claim 4 wherein benzyl 7β-phenylacetamido-3-acetoxymethyl-3-cephem-4-carboxylate is reacted.

7. The process of claim 4 wherein benzyl 7α-methoxy-7β-phenylacetamido-3-acetoxymethyl-3-cephem-4-carboxylate is reacted.

8. The process of claims 5, 6 or 7 carried out in the presence of a hydrogen iodide acceptor.

9. The process of claim 8 wherein the hydrogen iodide acceptor is propylene oxide or propene.

10. The process of claim 2 wherein R is a group of the formula R′—CH$_2$—.

11. The process of claim 10 wherein t-butyl 7β-(2-thienylacetamido)-3-acetoxymethyl-3-cephem-4-carboxylate is reacted.

12. The process of claim 10 wherein trimethylsilyl 7β-(2-thienylacetamido)-3-acetoxymethyl-3-cephem-4-carboxylate is reacted.

13. The process of claims 10, 11, or 12, carried out in the presence of a hydrogen iodide acceptor.

14. The process of claim 2 wherein R is

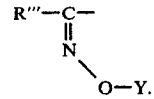

15. The process of claim 14 wherein methyl 7β-[syn-2-(2-tritylaminothiazol-4-yl)-2-methoxyiminoacetamido]-3-acetoxymethyl-3-cephem-4-carboxylate is reacted.

16. The process of claims 14 or 15 carried out in the presence of a hydrogen iodide acceptor.

17. The process of claim 2 wherein R is a group of the formula R′—CH$_2$— and $R_2$ is a carbamoyloxy group.

18. The process of claim 17 wherein methyl 7α-methoxy-7β-(2-thienylacetamido)-3-carbamoyloxymethyl-3-cephem-4-carboxylate is reacted.

19. The process of claim 2 for preparing a 3-iodomethyl cephalosporin trimethylsilyl ester wherein $R_1$ of the 3-alkanoyloxymethyl or 3-carbamoyloxymethyl cephalosporin is diphenylmethyl, p-methoxybenzyl, sodium or potassium, is reacted with at least 2 moles of trimethylsilyl iodide per mole of said ester or said salt.

20. The process of claim 19 wherein $R_1$ is diphenylmethyl or p-methoxybenzyl.

* * * * *